(12) United States Patent
Gilbert

(10) Patent No.: US 8,685,015 B2
(45) Date of Patent: Apr. 1, 2014

(54) SYSTEM AND METHOD FOR MULTI-POLE PHASE-SHIFTED RADIO FREQUENCY APPLICATION

(75) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1216 days.

(21) Appl. No.: 12/566,200

(22) Filed: Sep. 24, 2009

(65) Prior Publication Data
US 2011/0071518 A1 Mar. 24, 2011

(51) Int. Cl.
*A61B 18/12* (2006.01)

(52) U.S. Cl.
USPC .......................................................... 606/34

(58) Field of Classification Search
USPC ............................................. 606/32, 34, 41
See application file for complete search history.

(56) References Cited

U.S. PATENT DOCUMENTS

| | | |
|---|---|---|
| 3,495,584 A | 2/1970 | Schwalm |
| 3,826,263 A | 7/1974 | Cage et al. |
| 3,971,365 A | 7/1976 | Smith |
| 4,114,623 A | 9/1978 | Meinke et al. |
| 4,651,280 A | 3/1987 | Chang et al. |
| 4,727,874 A | 3/1988 | Bowers et al. |
| 4,767,999 A | 8/1988 | VerPlanck |
| 4,818,954 A | 4/1989 | Flachenecker et al. |
| 4,860,745 A | 8/1989 | Farin et al. |
| 4,922,210 A | 5/1990 | Flachenecker et al. |
| 5,108,391 A | 4/1992 | Flachenecker |
| 5,281,213 A | 1/1994 | Milder et al. |
| 5,300,070 A | 4/1994 | Gentelia |
| 5,370,645 A | 12/1994 | Klicek et al. |
| 5,372,596 A | 12/1994 | Klicek et al. |
| 5,383,874 A | 1/1995 | Jackson |
| 5,383,917 A | 1/1995 | Desai et al. |
| 5,414,238 A | 5/1995 | Steigerwald et al. |
| 5,423,808 A | 6/1995 | Edwards et al. |
| 5,430,434 A | 7/1995 | Lederer et al. |
| 5,438,302 A | 8/1995 | Goble |
| 5,540,682 A * | 7/1996 | Gardner et al. ................. 606/37 |
| 5,620,481 A | 4/1997 | Desai et al. |
| 5,651,780 A | 7/1997 | Jackson et al. |
| 5,693,078 A | 12/1997 | Desai et al. |
| 5,696,441 A | 12/1997 | Mak et al. |
| 5,722,975 A | 3/1998 | Edwards et al. |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

U.S. Appl. No. 10/406,690, Apr. 2003, Michael S. Klicek.*

(Continued)

*Primary Examiner* — Ronald Hupczey, Jr.

(57) ABSTRACT

An electrosurgical generator is disclosed. The generator includes a power supply operable to generate a DC voltage and a multi-pole, phase-shifted, pulse-width and/or frequency modulated RF output stage coupled to the power supply. The RF output stage includes a plurality of dual-pole circuits, each of the plurality of dual-pole circuits including first and second pairs of switching components. The generator also includes a controller configured to drive the first and second pairs of switching components of each of the plurality of dual-pole circuits at a predetermined phase-shifted frequency.

11 Claims, 6 Drawing Sheets

(56) References Cited

U.S. PATENT DOCUMENTS

| | | | |
|---|---|---|---|
| 5,743,903 A | 4/1998 | Stern et al. | |
| 5,817,093 A * | 10/1998 | Williamson et al. | 606/50 |
| 5,897,552 A | 4/1999 | Edwards et al. | |
| 5,971,980 A | 10/1999 | Sherman | |
| 6,007,532 A | 12/1999 | Netherly | |
| 6,063,078 A | 5/2000 | Wittkampf | |
| 6,074,386 A | 6/2000 | Goble et al. | |
| 6,142,992 A | 11/2000 | Cheng et al. | |
| 6,171,304 B1 | 1/2001 | Netherly et al. | |
| 6,193,713 B1 * | 2/2001 | Geistert et al. | 606/34 |
| 6,261,286 B1 | 7/2001 | Goble et al. | |
| 6,275,786 B1 | 8/2001 | Daners | |
| 6,293,942 B1 | 9/2001 | Goble et al. | |
| 6,306,134 B1 | 10/2001 | Goble et al. | |
| 6,309,386 B1 | 10/2001 | Bek | |
| 6,325,799 B1 | 12/2001 | Goble | |
| 6,364,877 B1 | 4/2002 | Goble et al. | |
| 6,416,509 B1 | 7/2002 | Goble et al. | |
| 6,423,057 B1 | 7/2002 | He et al. | |
| 6,485,487 B1 * | 11/2002 | Sherman | 606/34 |
| 6,696,844 B2 | 2/2004 | Wong et al. | |
| 6,730,080 B2 | 5/2004 | Harano | |
| 6,740,079 B1 | 5/2004 | Eggers | |
| 6,743,225 B2 | 6/2004 | Sanchez et al. | |
| 6,784,405 B2 | 8/2004 | Flugstad et al. | |
| 6,923,804 B2 | 8/2005 | Eggers et al. | |
| 6,929,641 B2 * | 8/2005 | Goble et al. | 606/37 |
| 6,962,587 B2 | 11/2005 | Johnson et al. | |
| 6,997,935 B2 * | 2/2006 | Anderson et al. | 606/169 |
| 7,066,933 B2 | 6/2006 | Hagg | |
| 7,115,124 B1 | 10/2006 | Xiao | |
| 7,151,964 B2 | 12/2006 | Desai et al. | |
| 7,172,591 B2 | 2/2007 | Harano et al. | |
| 7,300,435 B2 | 11/2007 | Wham et al. | |
| 7,407,502 B2 * | 8/2008 | Strul et al. | 606/34 |
| 7,425,835 B2 | 9/2008 | Eisele | |
| 7,648,494 B2 * | 1/2010 | Kornerup et al. | 604/539 |
| 8,113,057 B2 * | 2/2012 | Orszulak et al. | 73/662 |
| 8,257,350 B2 * | 9/2012 | Marion | 606/38 |
| 2004/0230189 A1 | 11/2004 | Keppel | |
| 2005/0004564 A1 | 1/2005 | Wham et al. | |
| 2006/0161148 A1 * | 7/2006 | Behnke | 606/34 |
| 2006/0224152 A1 | 10/2006 | Behnke et al. | |
| 2007/0093800 A1 | 4/2007 | Wham et al. | |
| 2007/0093801 A1 | 4/2007 | Behnke | |
| 2007/0225698 A1 | 9/2007 | Orszulak et al. | |
| 2008/0015564 A1 | 1/2008 | Wham et al. | |
| 2009/0254677 A1 * | 10/2009 | Desanti | 709/242 |
| 2009/0292283 A1 * | 11/2009 | Odom | 606/51 |
| 2009/0306648 A1 * | 12/2009 | Podhajsky et al. | 606/34 |
| 2009/0318915 A1 * | 12/2009 | Hosier et al. | 606/33 |
| 2010/0030210 A1 * | 2/2010 | Paulus | 606/38 |
| 2010/0057076 A1 * | 3/2010 | Behnke et al. | 606/35 |
| 2010/0063494 A1 * | 3/2010 | Orszulak | 606/33 |
| 2010/0063497 A1 * | 3/2010 | Orszulak | 606/35 |
| 2010/0079215 A1 * | 4/2010 | Brannan et al. | 333/1.1 |
| 2010/0082022 A1 * | 4/2010 | Haley et al. | 606/33 |
| 2010/0082023 A1 * | 4/2010 | Brannan et al. | 606/33 |
| 2010/0082024 A1 * | 4/2010 | Brannan et al. | 606/33 |
| 2010/0082025 A1 * | 4/2010 | Brannan et al. | 606/33 |
| 2010/0082083 A1 * | 4/2010 | Brannan et al. | 607/102 |
| 2010/0082084 A1 * | 4/2010 | Brannan et al. | 607/102 |
| 2010/0094271 A1 * | 4/2010 | Ward et al. | 606/33 |
| 2010/0094288 A1 * | 4/2010 | Kerr | 606/51 |
| 2010/0114090 A1 * | 5/2010 | Hosier | 606/33 |
| 2010/0179529 A1 * | 7/2010 | Podhajsky et al. | 606/33 |
| 2010/0179533 A1 * | 7/2010 | Podhajsky | 606/34 |
| 2010/0179534 A1 * | 7/2010 | Podhajsky et al. | 606/34 |
| 2010/0179535 A1 * | 7/2010 | Podhajsky et al. | 606/34 |
| 2010/0179536 A1 * | 7/2010 | Podhajsky et al. | 606/34 |
| 2010/0179541 A1 * | 7/2010 | Joseph et al. | 606/42 |
| 2010/0179542 A1 * | 7/2010 | Joseph et al. | 606/42 |
| 2011/0028963 A1 * | 2/2011 | Gilbert | 606/33 |
| 2011/0037484 A1 * | 2/2011 | Gilbert | 324/649 |
| 2011/0054460 A1 * | 3/2011 | Gilbert | 606/33 |
| 2011/0060329 A1 * | 3/2011 | Gilbert et al. | 606/34 |
| 2011/0071516 A1 * | 3/2011 | Gregg | 606/34 |
| 2011/0071521 A1 * | 3/2011 | Gilbert | 606/42 |
| 2011/0077631 A1 * | 3/2011 | Keller | 606/33 |
| 2011/0112530 A1 * | 5/2011 | Keller | 606/42 |

FOREIGN PATENT DOCUMENTS

| | | | |
|---|---|---|---|
| DE | 1139927 | 11/1962 | |
| DE | 1149832 | 6/1963 | |
| DE | 1439302 | 1/1969 | |
| DE | 2439587 | 2/1975 | |
| DE | 2455174 | 5/1975 | |
| DE | 2407559 | 8/1975 | |
| DE | 2602517 | 7/1976 | |
| DE | 2504280 | 8/1976 | |
| DE | 2540968 | 3/1977 | |
| DE | 2820908 | 11/1978 | |
| DE | 2803275 | 8/1979 | |
| DE | 2823291 | 11/1979 | |
| DE | 2946728 | 5/1981 | |
| DE | 3143421 | 5/1982 | |
| DE | 3045996 | 7/1982 | |
| DE | 3120102 | 12/1982 | |
| DE | 3510586 | 10/1986 | |
| DE | 3604823 | 8/1987 | |
| DE | 390937 | 4/1989 | |
| DE | 3904558 | 8/1990 | |
| DE | 3942998 | 7/1991 | |
| DE | 4339049 | 5/1995 | |
| DE | 19717411 | 11/1998 | |
| DE | 19848540 | 5/2000 | |
| EP | 246350 | 11/1987 | |
| EP | 310431 | 4/1989 | |
| EP | 325456 | 7/1989 | |
| EP | 336742 | 10/1989 | |
| EP | 390937 | 10/1990 | |
| EP | 556705 | 8/1993 | |
| EP | 608609 | 8/1994 | |
| EP | 836868 | 4/1998 | |
| EP | 1051948 | 11/2000 | |
| EP | 880220 | 6/2006 | |
| EP | 1681026 | 7/2006 | |
| EP | 1707144 | 10/2006 | |
| EP | 2100566 | 9/2009 | |
| FR | 1275415 | 10/1961 | |
| FR | 1347865 | 11/1963 | |
| FR | 2313708 | 12/1976 | |
| FR | 2364461 | 7/1978 | |
| FR | 2502935 | 10/1982 | |
| FR | 2517953 | 6/1983 | |
| FR | 2573301 | 5/1986 | |
| GB | 2154881 A * | 9/1985 | A61B 17/36 |
| SU | 166452 | 1/1965 | |
| SU | 727201 | 4/1980 | |
| WO | WO96/08794 | 3/1996 | |
| WO | WO96/39086 | 12/1996 | |
| WO | WO02/11634 | 2/2002 | |
| WO | WO02/45589 | 6/2002 | |
| WO | WO02/47565 | 6/2002 | |
| WO | WO03/090635 | 11/2003 | |
| WO | WO 2004/043240 | 5/2004 | |
| WO | WO2004/098385 | 11/2004 | |
| WO | WO2005/046496 | 5/2005 | |
| WO | WO2006/050888 | 5/2006 | |
| WO | WO 2006/050888 | 5/2006 | |
| WO | WO 2008101356 | 8/2008 | |

OTHER PUBLICATIONS

U.S. Appl. No. 10/573,713, Mar. 2006, Robert Wham.*
U.S. Appl. No. 11/242,458, Oct. 2005, Daniel Becker.*
International Search Report from EP Appl. No. 11186103.5 dated Sep. 19, 2012.
U.S. Appl. No. 10/406,690, filed Apr. 3, 2003.
U.S. Appl. No. 10/573,713, filed Mar. 28, 2006.
U.S. Appl. No. 11/242,458, filed Oct. 3, 2005.
U.S. Appl. No. 12/136,620, filed Jun. 10, 2008.
U.S. Appl. No. 12/184,556, filed Aug. 1, 2008.

(56) References Cited

OTHER PUBLICATIONS

U.S. Appl. No. 12/203,734, filed Sep. 3, 2008.
U.S. Appl. No. 12/205,298, filed Sep. 5, 2008.
U.S. Appl. No. 12/205,525, filed Sep. 5, 2008.
U.S. Appl. No. 12/241,861, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
U.S. Appl. No. 12/242,026, filed Sep. 30, 2008.
U.S. Appl. No. 12/242,061, filed Sep. 30, 2008.
U.S. Appl. No. 12/242,102, filed Sep. 30, 2008.
U.S. Appl. No. 12/249,218, filed Oct. 10, 2008.
U.S. Appl. No. 12/249,263, filed Oct. 10, 2008.
U.S. Appl. No. 12/351,935, filed Jan. 12, 2009.
U.S. Appl. No. 12/351,947, filed Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/407,896, filed Mar. 20, 2009.
U.S. Appl. No. 12/477,245, filed Jun. 3, 2009.
U.S. Appl. No. 12/481,087, filed Jun. 9, 2009.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
European Search Report for European Application No. 10179305 dated Aug. 23, 2011.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09164754.5 dated Aug. 21, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US09/46870 dated Jul. 21, 2009.

* cited by examiner

SYSTEM AND METHOD FOR MULTI-POLE PHASE-SHIFTED RADIO FREQUENCY APPLICATION

BACKGROUND

1. Technical Field

The present disclosure relates to electrosurgical apparatuses, systems and methods. More particularly, the present disclosure is directed to electrosurgical multi-polar electrosurgical systems.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue.

In bipolar electrosurgery, one of the electrodes of the handheld instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

Bipolar electrosurgical techniques and instruments can be used to coagulate blood vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

In monopolar electrosurgery, the active electrode is typically a part of the surgical instrument held by the surgeon that is applied to the tissue to be treated. A patient return electrode is placed remotely from the active electrode to carry the current back to the generator and safely disperse current applied by the active electrode. The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle. In bipolar and monopolar modes, it is desirable to utilize more than one active electrode to achieve desired ablation and lesion formation.

SUMMARY

According to one embodiment of the present disclosure, an electrosurgical generator is disclosed. The generator includes a power supply operable to generate a DC voltage and a multi-pole phase-shifted RF output stage coupled to the power supply. The RF output stage includes a plurality of dual-pole circuits, each of the plurality of dual-pole circuits including first and second pairs of switching components. The generator also includes a controller configured to drive the first and second pairs of switching components of each of the plurality of dual-pole circuits at a predetermined phase-shifted frequency.

According to another embodiment of the present disclosure an electrosurgical system is disclosed. The system includes an electro surgical generator having a power supply operable to generate a DC voltage. The generator also includes a multi-pole, phase-shifted, pulse-width and/or frequency modulated RF output stage coupled to the power supply. The RF output stage includes an isolation transformer having a secondary winding and a plurality of dual-pole circuits having first and second pairs of switching components and a primary winding coupled to the secondary winding. The generator further includes a controller configured to drive the first and second pairs of switching components of each of the plurality of dual-pole circuits at a predetermined phase-shifted frequency to generate a waveform crest at each of the output terminals. The system also includes a plurality of active electrodes, each of which is coupled to each of the output terminals.

According to a further embodiment of the present disclosure an electrosurgical system is disclosed. The system includes an electrosurgical generator having a power supply operable to generate a DC voltage. The generator includes a multi-pole, phase-shifted, pulse-width and/or frequency modulated RF output stage coupled to the power supply. The RF output stage includes a plurality of dual-pole circuits, each of the plurality of dual-pole circuits including first and second pairs of switching components, the RF output stage further includes an isolation transformer having a secondary winding and wherein each of the plurality of dual-pole circuits includes a primary winding coupled to the secondary winding. The generator also includes a controller configured to drive the first and second pairs of switching components of each of the plurality of dual-pole circuit at a predetermined phase-shifted frequency. The system includes a plurality of active electrodes, each of which is coupled to each of the output terminals.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, multi-polar ablation needles, etc.). Further, the generator includes electronic circuitry configured for generating radio frequency power specifically suited for various electrosurgical modes (e.g., cutting, blending, division, ablation etc.) and procedures (e.g., monopolar, bipolar, vessel sealing, ablation).

Figure 1:
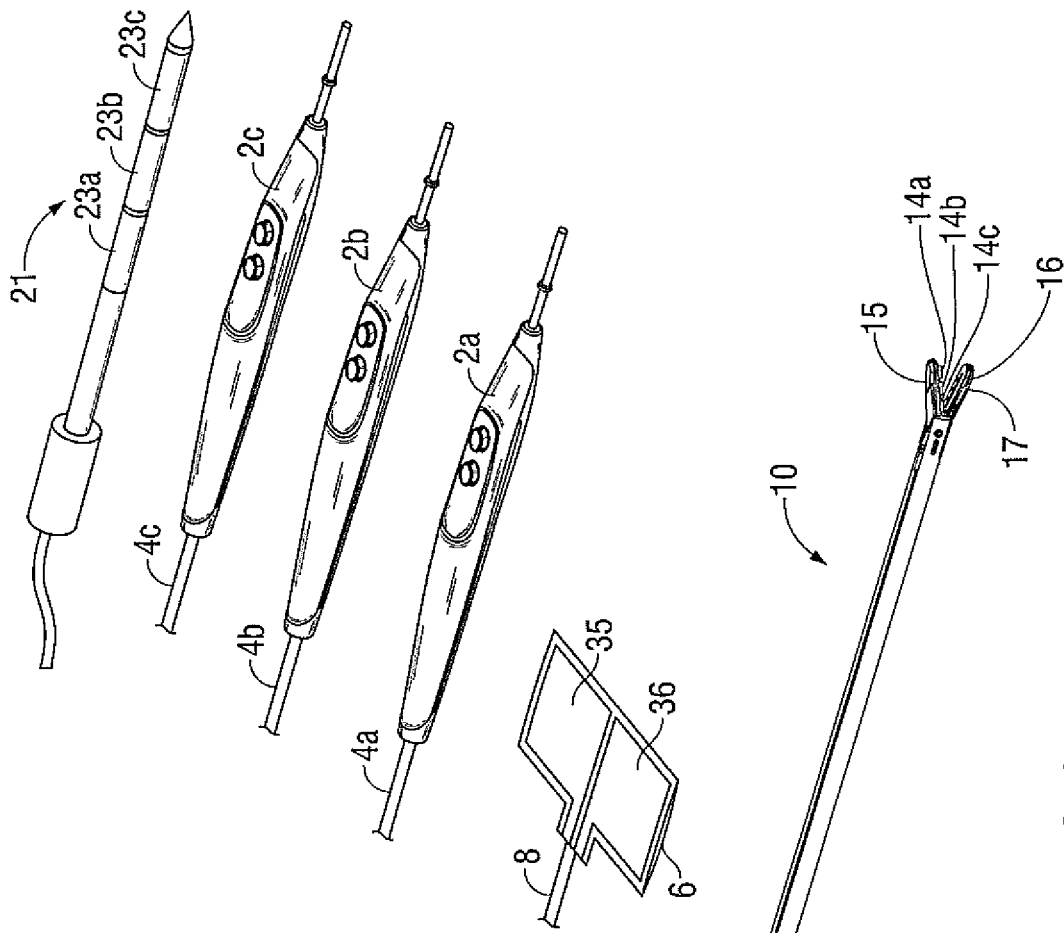
FIG. 1 is a perspective view of an electrosurgical system according to one embodiment of the present disclosure.
Figure 1:
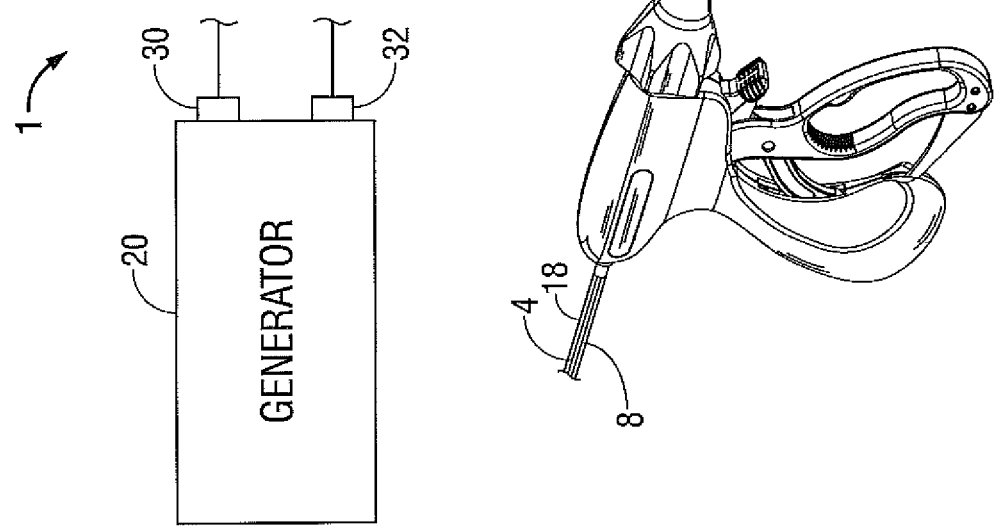

FIG. 1 is a schematic illustration of a bipolar and monopolar electrosurgical system 1 according to one embodiment of the present disclosure. The system 1 includes one or more monopolar electrosurgical instruments 2a, 2b, 2c, etc. having one or more electrodes for treating tissue of a patient (e.g., electrosurgical cutting probe, ablation electrode(s), etc.). Electrosurgical RF energy is supplied to the instruments 2a, 2b, 2c by a generator 20 via a corresponding supply line 4a, 4b, 4c, etc., that is connected to an active terminal 30 (FIG. 2) of the generator 20, allowing the instruments 2a, 2b, 2c to coagulate, ablate and/or otherwise treat tissue. The energy is returned to the generator 20 through a return electrode 6 via a return line 8 at a return terminal 32 (FIG. 2) of the generator 20. The system 1 may include a plurality of return electrodes 6 that are arranged to minimize the chances of tissue damage by maximizing the overall contact area with the patient. In addition, the generator 20 and the return electrode 6 may be configured for monitoring so-called "tissue-to-patient" contact to insure that sufficient contact exists therebetween to further minimize chances of tissue damage. In another embodiment, the system 1 also includes a multi-polar ablation device 21 having a plurality of electrodes 23a, 23b, 23c, etc.

The system 1 also includes a bipolar electrosurgical forceps 10 having one or more pairs of electrodes for treating tissue of a patient. The electrosurgical forceps 10 include opposing jaw members 15, 17 having one or more active electrodes 14a, 14b, 14c, etc. and a return electrode 16 disposed therein, respectively. The active electrodes 14a, 14b, 14c and the return electrode 16 are connected to the generator 20 through cable 18, which includes the supply and return lines 4, 8 coupled to the active and return terminals 30, 32, respectively. The electrosurgical forceps 10 are coupled to the generator 20 at a connector having connections to the active and return terminals 30 and 32 (e.g., pins) via a plug disposed at the end of the cable 18, wherein the plug includes contacts from the supply and return lines 4, 8.

The generator 20 may be any suitable type (e.g., electrosurgical, microwave, etc.) and may include a plurality of connectors to accommodate various types of electrosurgical instruments (e.g., multiple instruments 2a, 2b, 2c, electrosurgical forceps 10, etc.). Further, the generator 20 is configured to operate in a variety of modes such as ablation, monopolar and bipolar cutting coagulation, etc. The generator 20 includes suitable input controls (e.g., buttons, activators, switches, touch screen, etc.) for controlling the generator 20. In addition, the generator 20 may include one or more display screens (not shown) for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, tissue sealing, ablating, intensity setting, etc.).

Figure 2:
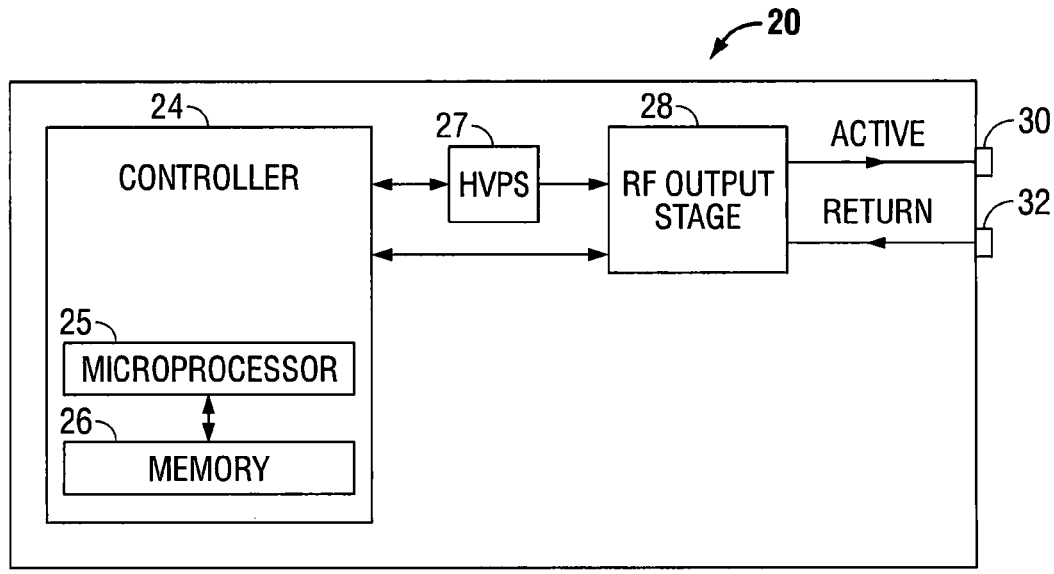
FIG. 2 is a schematic block diagram of a generator according to an embodiment of the present disclosure.

FIG. 2 shows a schematic block diagram of the generator 20 having a controller 24, a high voltage DC power supply 27 ("HVPS") and an RF output stage 28. The HVPS 27 is connected to an AC source (e.g., electrical wall outlet) and provides high voltage DC power to an RF output stage 28, which then converts high voltage DC power into RF energy and delivers the RF energy to the active terminal 30. The energy is returned thereto via the return terminal 32. In particular, the RF output stage 28 generates sinusoidal or rectangular waveforms of high RF energy. The RF output stage 28 is configured to generate a plurality of waveforms having various duty cycles, peak voltages, waveform crest factors, and other suitable parameters. Certain types of waveforms are suitable for specific electrosurgical modes. For instance, the RF output stage 28 typically generates a 100% duty cycle sinusoidal waveform in cut mode, which is well-suited for ablating, fusing and dissecting tissue and a 1-25% duty cycle waveform in coagulation mode, which is best used for cauterizing tissue to stop bleeding.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop, in which a plurality of sensors measure a variety of tissue and energy properties (e.g., tissue impedance, tissue temperature, output current and/or voltage, etc.), and provide feedback to the controller 24. Such sensors are within the purview of those skilled in the art. The controller 24 then signals the HVPS 27 and/or RF output stage 28, which then adjust DC and/or RF output power, respectively. The controller 24 also receives input signals from the input controls of the generator 20, the instruments 2a, 2b, 2c or forceps 10. The controller 24 utilizes the input signals to adjust power outputted by the generator 20 and/or performs other control functions thereon.

Figure 3A:
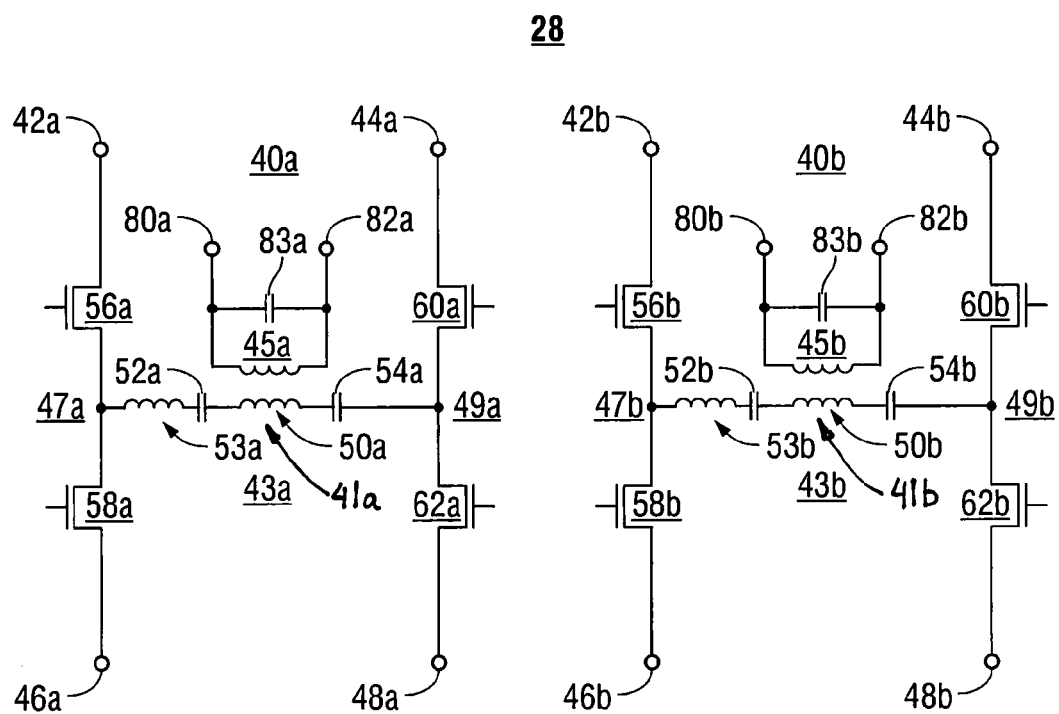
FIGS. 3A-3B are schematic circuit diagrams of a multi-pole phase-shifted radio frequency output stage according to an embodiment of the present disclosure.
Figure 3B:
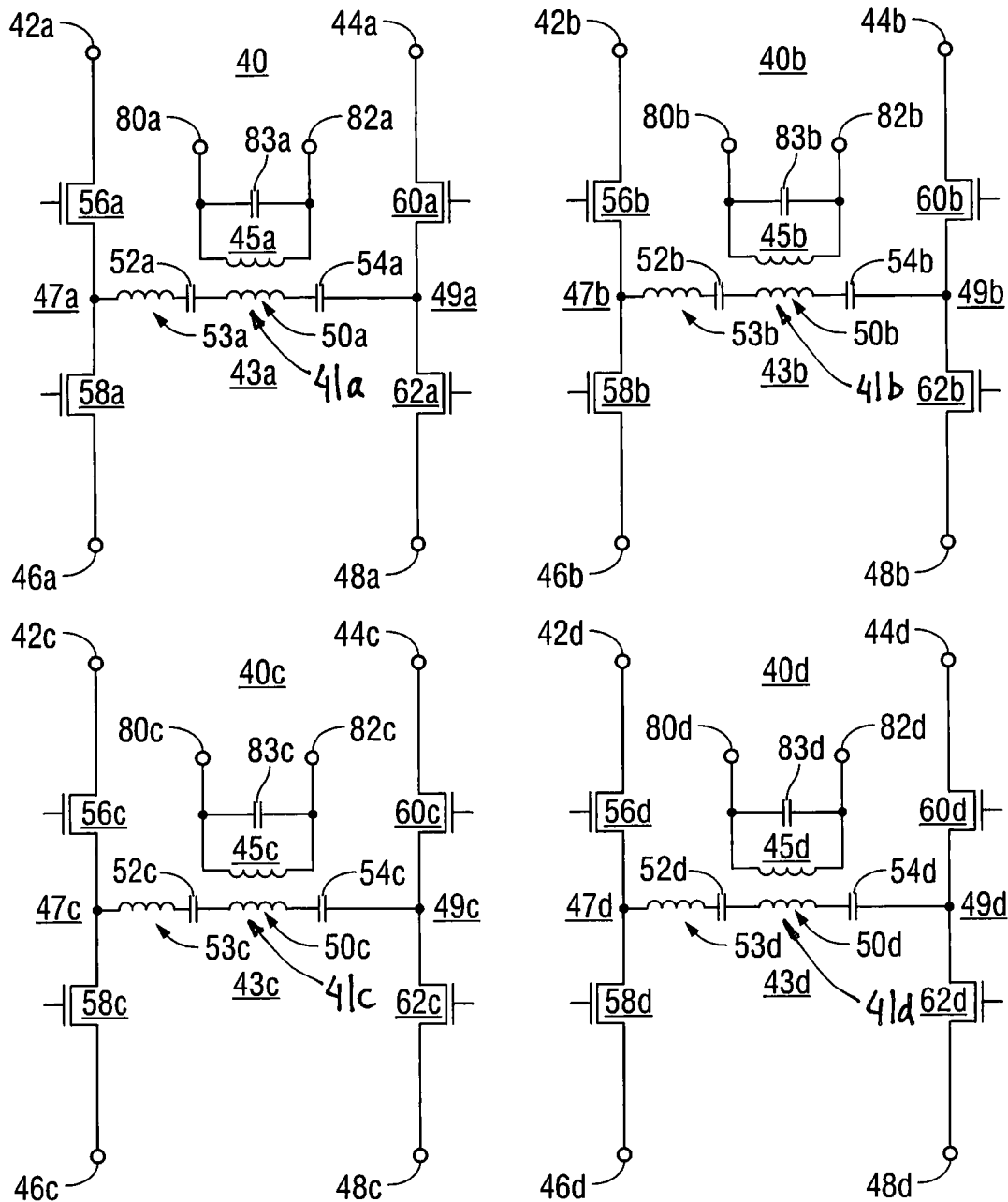

The RF output stage 28 is a multi-pole, phase-shifted, pulse-width and/or frequency modulated RF inverter as shown in more detail in FIGS. 3a and 3B. As shown in FIG. 3A, the RF output stage 28 includes two or more dual-pole circuits 40a and 40b (e.g., bridge circuit). Each of the dual-pole circuits 40a and 40b is coupled to the HVPS 27 and receives DC voltage therefrom. More specifically, each of the dual-pole assemblies 40a and 40b includes an isolation transformer 41a and 41b, respectively. Each of the isolation transformers 41a and 41b includes a primary winding 43a, 43b and a secondary winding 45a, 45b, respectively. The primary windings 43a and 43b include first and second connections 47a, 49a and 47b, 49b, respectively. The first connections 47a, 47b include drain supplies 42a, 42b and source supplies 46a, 46b, respectively. The second connections 49a, 49b also include drain supplies 44a, 44b and source supplies 48a, 48b, respectively. The source supplies 46a, 48a, 46b, 48b and drain supplies 42a, 44a, 42b, 44b are coupled to the HVPS 27.

First connection 47a includes a first pair of switching components 56a and 58a and second connection 49a includes a second pair of switching components 60a and 62a, respectively. First and second connections 47b and 49b also include first and second pairs of switching components 56b, 58b and 60b, 62b, respectively. The switching components 56a, 58a, 60a, 62a and 56b, 58b, 60b, 62b can be, for example, transistors, such as metal-oxide semiconductor field-effect transistors (MOSFET), insulated gate bipolar transistors (IGBT), relays, and the like.

The secondary windings 45a, 45b include two output terminals 80a, 82a, 80b, 82b, respectively. Each pair of the output terminals 80a, 82a, 80b, 82b includes a band pass filter 83a and 83b coupled therebetween. The first and second connections 47a and 49a are connected in series by a resonant network 50a. The resonant network 50a may be a series resonant network that is arranged in an LCC configuration having an inductor 53a and capacitors 52a and 54a with the primary winding 43a being coupled between capacitors 52a and 54a. The first and second connections 47b and 49b are similarly connected in series by a resonant network 50b with the primary winding 43b coupled between capacitors 52b and 54b. In one embodiment, the resonant networks 50a and 50b may be parallel resonant networks and may include a plurality of reactive and passive components.

Output terminals 80a, 82a and 80b, 82b may be separately connected to multiple active and return pole pairs of monopolar, bipolar electrosurgical or ablation instruments (e.g., instruments 2a, 2b, 2c, electrodes 23a, 23b, 23c or active electrodes 14a, 14b, 14c). Additionally or alternatively, output terminals 80a, 82a and 80b, 82b may share connections to a single active or return lead. In one embodiment, output terminals 82a and 82b are coupled to the return electrode 6, while output terminals 80a and 80b are coupled to active leads on either a single or multiple instruments. This configuration allows for simultaneous activation of instruments or multi-pole pairs of the same instrument (e.g., device 21).

With respect to FIG. 3B, another embodiment of the RF output stage 28 is shown. The RF output stage 28 includes four dual-pole circuits 40a, 40b, 40c and 40d. Each of the dual-pole circuits 40c and 40d is substantially similar to the dual-pole circuits 40a and 40b and is also coupled to the HVPS 27 and receives DC voltage therefrom. Each of the dual-pole circuits 40c and 40d includes an isolation transformer 41c and 41d, respectively. Each of the isolation transformers 41c and 41d includes a primary winding 43c, 43d and a secondary winding 45c, 45d. The primary windings 43c and 43d include first and second connections 47c, 49c and 47d, 49b, respectively. The first connections 47c, 47d include drain supplies 42c, 42d and source supplies 46d, 46c, respectively. The second connections 49c, 49d also includes a drain supply 44c, 44d and source supplies 48c, 48d, respectively. The source supplies 46c, 48c, 46d, 48d and drain supplies 42c, 44c, 42d, 44d are coupled to the HVPS 27.

The first connection 47c includes a first pair of switching components 56c and 58c and the second connection 49c includes a second pair of switching components 60c and 62c, respectively. The first and second connections 47d and 49d also include first and second pairs of switching components 56d, 58b and 60d, 62d, respectively. The switching components 56c, 58c, 60c, 62c and 56d, 58b, 60d, 62d can be, for example, transistors, such as metal-oxide semiconductor field-effect transistors (MOSFET), insulated gate bipolar transistors (IGBT), relays, and the like.

The secondary windings 45c, 45d include two output terminals 80c, 82c, 80d, 82d, respectively. Each pair of the output terminals 80c, 82c, 80d, 82d includes a band pass filter 83c and 83d coupled therebetween. The first and second connections 47c and 49c are connected in series by a resonant network 50c having an inductor 53c and capacitors 52c and 54c arranged in a LCC configuration with the primary winding 43c. The first and second connections 47d and 49d are similarly connected in series by a resonant network 50d having an inductor 53d with the primary winding 43d coupled between capacitors 52b and 54b. In one embodiment, the resonant networks 50c and 50d may be parallel resonant networks and may include a plurality of reactive and passive components.

The operation of the RF output stage 28 is described with respect to FIG. 3A since the operation of four dual-pole circuits 40a, 40b, 40c, 40d of FIG. 3B is substantially similar to that of two dual-pole circuits 40a and 40b. The switching components 56a, 58a, 60a, 62a, 56b, 58b, 60b, 62b are coupled to the controller 24. The controller 24 drives the switching components 56a, 58a, 60a, 62a, 56b, 58b, 60b, 62b at a predetermined frequency or frequencies to turn "on" and "off" at a range of predetermined frequencies which is also the operating frequency range of the generator 20, thereby closing and opening the first and second connections 47a, 47b and 49a, 49b, respectively. The frequency at which the switching components 56a, 58a, 60a, 62a, 56b, 58b, 60b, 62b are turned on and off is controlled by the controller 24. The controller 24 may include a pulse-width modulated driver for supplying a driver signal to each of the switching components 56a, 58a, 60a, 62a, 56b, 58b, 60b, 62b. The driver emits a phase-shifted drive signals having first and second components that are out of phase (e.g., 180° out-of-phase). Thus, each pair of the switching components (e.g., 56a and 58a, 60a and 62a, 56b and 58b, 60b and 62b) has a phase relationship 180° out-of-phase with its opposing pair. In other words, the driver signal cycles each of the pairs of the switching components 56a, 58a, 60a, 62a, 56b, 58b, 60b, 62b between "on" and "off" positions at the same frequency but out of sync, to create two waveforms 180° out-of-phase at each first and second connections 47a, 49a, 47b, 49b. In addition, the drive signals to each pair of the switching components 56a, 58a, 60a, 62a, 56b, 58b, 60b, 62b are also phase-shifted with respect to each other to generate a plurality of waveforms of varying duty cycle. Therefore, adjusting the phase-shifted dual drive signals provides varying operating RF duty cycles or pulse-widths. Varying the duty cycle of the phase-shifted dual drive signals allows for better control of the RF amplitude and the average power delivered. Phase-shifting also allows for interleaving of power delivered to the various output terminal pairs (e.g., 80a and 82a). Further, when combined with a resonant network (e.g., resonant network 50a), the pulse-width or frequency modulation may be used to vary the output amplitude at the load.

The resonant networks 50a and 50b in combination with the primary windings 43a and 43b convert rectangular pulse-width modulate (e.g., AC energy having multiple high frequency components) energy into RF energy (e.g., AC energy having a single high frequency component from about 100 kHz to about 100,000 kHz). When the switching components 56a, 58a, 60a, 62a, 56b, 58b, 60b, 62b are closed, a high frequency pulse is supplied to the capacitors 52a, 54a, 52b, 54b of the resonant networks 50a and 50b. The resonant networks 50a and 50b convert the pulses into biphasic sinusoidal waveforms by the alternation of first and second connections 47a, 47b and 49a, 49b respectively. The resonant circuits 50a and 50b can include a plurality of active components (e.g., inductors and capacitors) arranged in either parallel, series or combination thereof.

During operation, primary windings 43a and 43b create two half-sinusoidal waveforms of the same frequency, but with variable phase with respect to each other, which then combine at a secondary windings 45a and 45b to form a full waveform. More specifically, each pair of the switching components 56a and 58a, 60a and 62a, 56b and 58b, 60b and 62b is driven by a drive signal supplied at a predetermined phase with respect to each other. Each pair of the switching components 56a and 58a, 60a and 62a, 56b and 58b, 60b and 62b is alternately switched "on" and "off" at the same frequency by the phase-shifted drive signals.

Figure 4A:
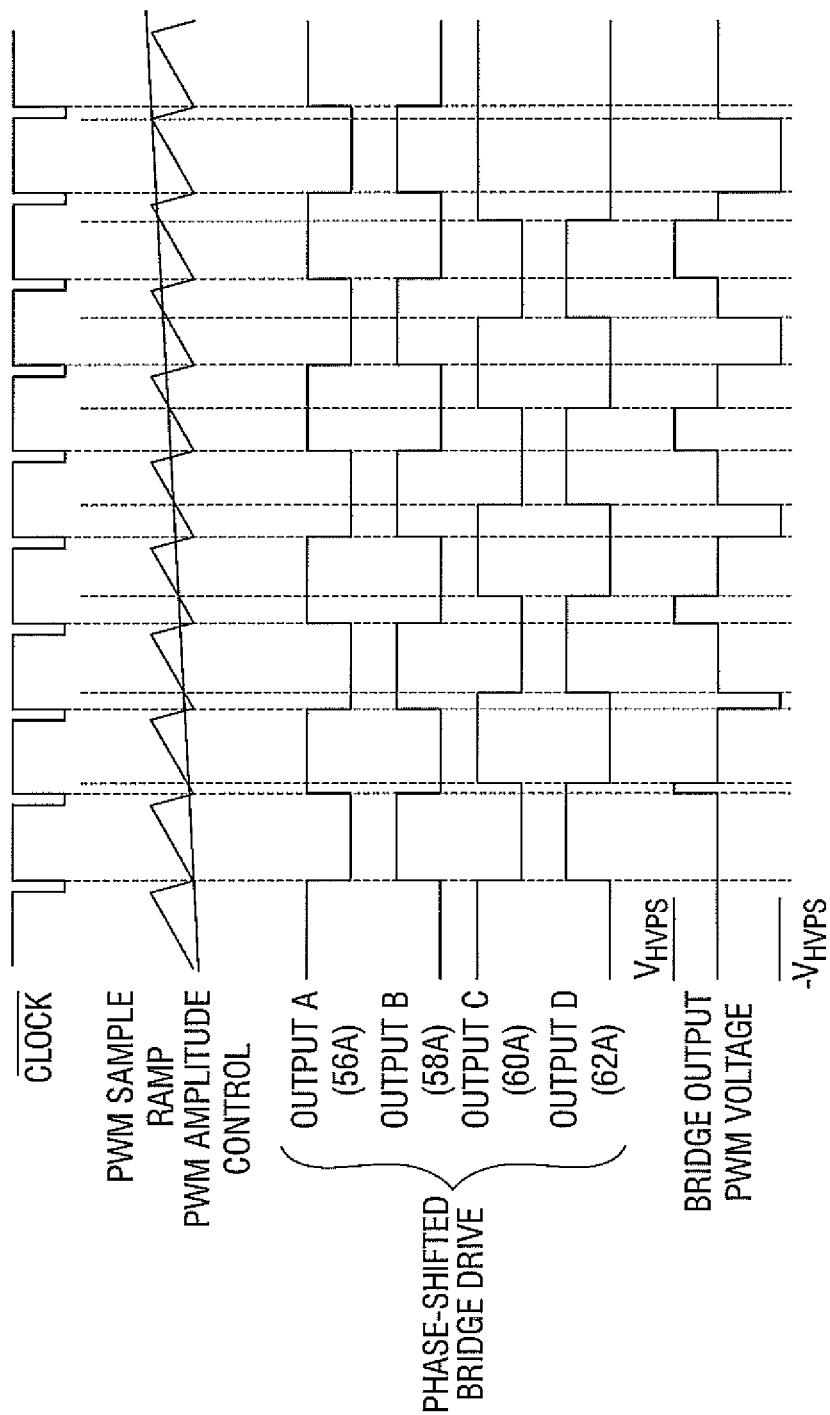
FIGS. 4A-4D illustrate a plurality of waveform cycles generated by the multi-pole phase-shifted radio frequency output stage of FIGS. 3A-3B according to an embodiment of the present disclosure.
Figure 4B:
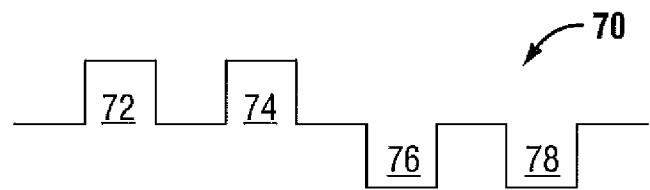
Figure 4C:
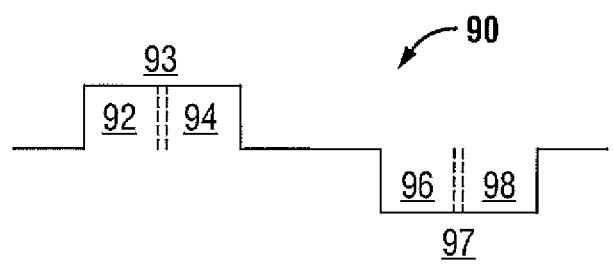

FIGS. 4A-4C show an output current produced by driving the first and second connections 47a, 47b and 49a, 49b of FIG. 3A at different phases. FIG. 4A shows the fundamental amplitude control for the dual-pole circuit 40a. FIGS. 4B and C show a single cycle of the current waveform as a rectangular waveform. The output waveform may have any waveform crest factor (e.g., sinusoidal) and the rectangular waveform is used for illustrative purposes.

FIG. 4A illustrates that the two phases may be driven in synchrony, while the outputs may be connected to a common return pad, common active electrode, or separate pole pairs of a multi-polar instrument. More specifically, FIG. 4A shows one embodiment of a phase-shifted pulse-width modulated drive for each of the switching components 56a, 58a, 60a, 62a. This controls the average or root mean square ("RMS") output amplitude. The resulting waveform is rectangular. If the bridge circuit (e.g., dual-pole circuit 40a) employs an LCC or any other type of resonant network (e.g., resonant network 50a), then the output waveform is going to sinusoidal. In embodiments, various arbitrary-in-phase synchrony can be utilized to create the other waveforms illustrated in FIGS. 4B-4D.

With reference to FIG. 4B, a single waveform cycle 70 is shown having a plurality of waveform crests 72, 74, 76, 78 that are generated by activating the first and second connections 47a, 47b and 49a, 49b, at different phases. The waveform crest 72 is generated by the switching components 56a and 62a being supplied a first activation pulse for a duration $Ton_a$. The switching components 56a and 62a are deactivated during a first deactivation period $Toff_a$, during which time the switching components 56b and 62b are activated by a second activation pulse for a duration $Ton_b$ to generate the waveform crest 74. In other words, the waveform crests 72 and 74 are achieved by activating the switching components 56a and 62a by the first activation pulse at a first phase (e.g., $\phi_a$) and the switching components 56b and 62b by the second activation pulse at a second phase (e.g., $\phi_b$).

The switching components 56b and 62b are deactivated during a second deactivation period $Toff_b$, during which time the switching components 58a and 60a are activated by a third activation pulse for a duration $Ton_c$ to generate the waveform crest 76. The switching components 58a and 60a are then deactivated during a third deactivation period $Toff_c$, during which time the switching components 58b and 60b are activated by a fourth activation pulse for a duration $Ton_d$ to generate the waveform crest 78. The switching components 58b and 60b are then deactivated during a fourth deactivation period $Toff_d$, during which time the cycle 70 repeats and the waveform crest 72 is generated by the switching components 56a and 62a being supplied the first activation pulse. The waveform crests 76 and 78 are achieved by activating the switching components 58a and 60a at a third phase (e.g., $\phi_c$) and the switching components 58b and 60b at a fourth phase (e.g., $\phi_d$). The drive signals are supplied to the switching components of the first and second connections 47a, 47b and 49a, 49b are phase-shifted. In one embodiment, $\phi_a$ may be 0°, $\phi_b$ may be 90°, $\phi_c$ may be 180° and $\phi_d$ may be 270°. More specifically, the first and second phases are 180° out-of-phase with the third and fourth phases, respectively.

Each of the waveform crests 72, 74, 76, 78 may be supplied individually to each of the output terminals 80a, 82a, 80b, 82b. This allows for generation of multi-polar phase-shifted application of RF energy through a plurality of poles (e.g., instruments 2a, 2b, 2c and return electrode 6 or active electrodes 14a, 14b, 14c and to the return electrode 16) by coupling each of the poles to the corresponding output terminals 80a, 82a, 80b, 82b.

FIG. 4C illustrates another embodiment of the present disclosure, in which two of the first and second connections 47a, 47b and 49a, 49b are driven in parallel or partially in parallel. FIG. 4C shows a single waveform cycle 90 is shown having a plurality of waveform crests 92, 93, 94, 96, 97, 98 that are generated by activating the first and second connections 47a, 47b and 49a, 49b, at different phases. The waveform crest 92 is generated by the switching components 56a and 62a being supplied a first activation pulse for a duration $Ton_a$, during which time the switching components 56b and 62b are activated by a second activation pulse for a duration $Ton_b$ to generate the waveform crest 94. The first and second activation pulses overlap at least partially, such that the resulting waveform crests 92 and 94 form a single waveform crest 93. The waveform crests 92 and 94 are achieved by activating the switching components 56a and 62a by the first activation pulse at a first phase (e.g., $\phi_a$) and the switching components 56b and 62b by the second activation pulse at a second phase (e.g., $\phi_b$).

The switching components 56a, 56b and 62a, 62b are deactivated during a second deactivation period $Toff_b$, during which time the switching components 58a and 60a are activated by a third activation pulse for a duration $Ton_c$ to generate the waveform crest 96. The switching components 58b and 60b are activated by a fourth activation pulse for a duration $Ton_d$ to generate the waveform crest 98. The third and fourth activation pulses overlap at least partially, such that the resulting waveform crests 96 and 98 form a single waveform crest 97. The waveform crests 96 and 98 are achieved by activating the switching components 56a and 62a at a third phase (e.g., $\phi_c$) and the switching components 58b and 60b at a fourth phase (e.g., $\phi_d$). The drive signals activating the switching components 58a, 58b, 56a, 56b, 62a, 62b, 60a, 60b are also phase-shifted to provide for multiple overlapping waveforms having waveform crests 92, 96 and 94, 98.

With reference to FIGS. 1 and 3B, the output terminals 80a, 82a, 80b, 82b, 80c, 82c, 80d, 82d of the dual-pole circuits 40a, 40b, 40c and 40d are coupled to the active and return terminals 30, 32 for outputting electrosurgical energy to the patient. In monopolar configuration, each of the output terminals 80a, 82a, 80b, 82b, 80c, 82c, 80d, 82d may be coupled individually to instruments 2a, 2b, 2c, etc. and to the return electrode 6 to provide for the return flow of the electrosurgical energy. In bipolar configuration, each of the output terminals 80a, 82a, 80b, 82b, 80c, 82c, 80d, 82d may be coupled individually to active electrodes 14a, 14b, 14c, etc. and to the return electrode 16.

Figure 4D:
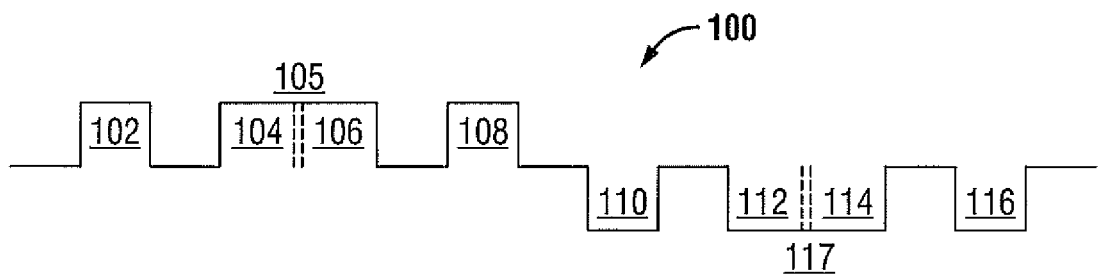

With reference to FIG. 4D, a single waveform cycle 100 is shown having a plurality of waveform crests 102, 104, 105, 106, 108, 110, 112, 113, 114, 116 that are generated by activating the first and second connections 47a, 47b, 47c, 47d and 49a, 49b, 49c, 49d at different phases. The waveform crest 102 is generated by the switching components 56a and 62a being supplied a first activation pulse for a duration $Ton_a$. The switching components 56a and 62a are deactivated during a first deactivation period $Toff_a$, during which time the waveform crest 105 is generated. The waveform crest 104 is generated by the switching components 56c and 62c being supplied a second activation pulse for a duration $Ton_b$, during which time the switching components 58d and 60d are activated by a third activation pulse for a duration $Ton_c$ to generate the waveform crest 106. The first and second activation pulses overlap at least partially, such that the resulting waveform crests 104 and 106 form the waveform crest 105. The switching components 56c, 56d and 62c, 62d are deactivated during a second deactivation period Toff$_b$, during which time the switching components 56b and 62b are activated by a fourth activation pulse for a duration Ton$_d$ to generate the waveform crest 108.

The switching components 56b and 62b are deactivated during a third deactivation period Toff$_c$, during which time the switching components 58a and 60a are activated by a fifth activation pulse for a duration Ton$_e$ to generate the waveform crest 110. The switching components 58a and 60a are then deactivated during a fourth deactivation period Toff$_d$, during which time the waveform crest 113 is generated. The switching components 58c and 60c are activated by a sixth activation pulse for a duration Ton$_f$ to generate the waveform crest 112. The switching components 58d and 60d are activated by a seventh activation pulse for a duration Ton$_g$ to generate the waveform crest 114. The sixth and seventh activation pulses overlap at least partially, such that the resulting waveform crests 112 and 114 form a single waveform crest 113. The switching components 58c, 58d and 60c, 60d are deactivated during a fifth deactivation period Toff$_e$, during which time the switching components 58b and 60b are activated by an eighth activation pulse for a duration Ton$_h$ to generate the waveform crest 116.

The waveform crest 102 is generated by activating the switching components 56a and 62a at a first phase (e.g., $\phi_a$). The waveform crests 104 and 106 are achieved by activating the switching components 56c and 62c by the first activation pulse at a second phase (e.g., $\phi_b$) and the switching components 56d and 62d by the second activation pulse at a third phase (e.g., $\phi_c$). The waveform crest 108 is generated by activating the switching components 56b and 62b at a fourth phase (e.g., $\phi_d$). The waveform crest 110 is generated by activating the switching components 58a and 60a at a fifth phase (e.g., $\phi_e$). The waveform crests 112 and 114 are achieved by activating the switching components 58c and 60c by the sixth activation pulse at a sixth phase (e.g., $\phi_f$) and the switching components 58d and 60d by the second activation pulse at a seventh phase (e.g., $\phi_g$). The waveform crest 116 is generated by activating the switching components 56b and 62b at an eighth phase (e.g., $\phi_h$). The drive signals are phase-shifted to provide for multiple waveform crests 102, 104, 106, 108, 110, 112, 114, 116. In one embodiment, the phases may be 45° apart, (e.g., $\phi_a$ may be 0°, $\phi_b$ may be 45°, $\phi_c$ may be 90°, $\phi_d$ may be 135°, $\phi_e$ may be 180°, $\phi_f$ may be 225°, $\phi_g$ may be 270°, $\phi_h$ may be)315°. More specifically, the first and fourth phases, the second and fifth, the third and sixth and the fourth and eighth phases are 180° out-of-phase.

Each of the waveform crests 102, 104, 106, 108, 110, 112, 114, 116 may be supplied individually to each of the output terminals 80a, 82a, 80b, 82b, 80c, 82c, 80d, 82d. This allows for generation of multi-polar phase-shifted application of RF energy through a plurality of poles (e.g., instruments 2a, 2b, 2c and return electrode 6 or active electrodes 14a, 14b, 14c and to the return electrode 16) by coupling each of the poles to the corresponding output terminals 80a, 82a, 80b, 82b, 80c, 82c, 80d, 82d.

Figure 5:
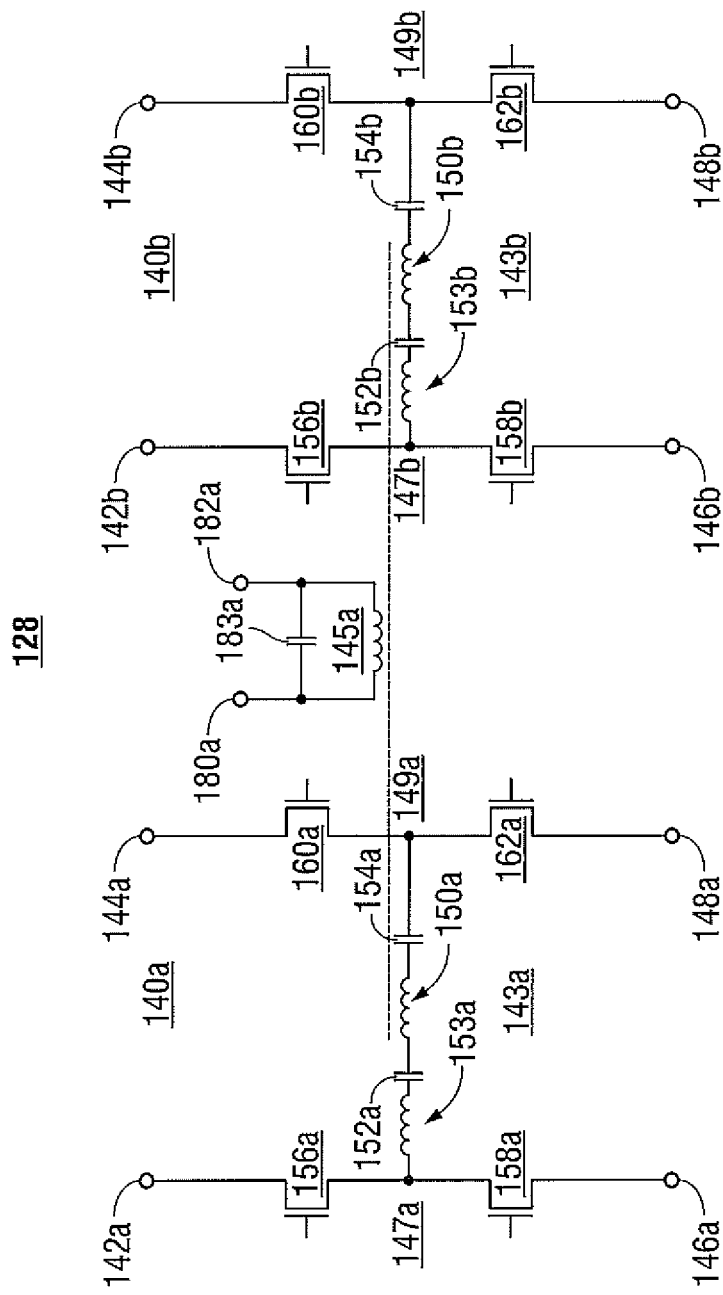
FIG. 5 is a schematic circuit diagram of a multi-pole phase-shifted radio frequency output stage according to an embodiment of the present disclosure.

FIG. 5 shows another embodiment of an output stage 228. The output stage 228 includes two or more dual-pole circuits 140a and 140b. Each of the dual-pole circuits 140a and 140b is coupled to the HVPS 27 and receives DC voltage therefrom. More specifically, each of the dual-pole assemblies 140a and 140h includes an isolation transformer 141a and 141b, respectively. Each of the isolation transformers 141a and 141b includes a primary winding 143a, 143b coupled to a single secondary winding 145. The primary windings 143a and 143b include first and second connections 147a, 149a and 147b, 149b, respectively. The first connections 147a, 147b include drain supplies 142a, 142b and source supplies 146a, 146b, respectively. The second connections 149a, 149b also includes a drain supply 144a, 144b and source supplies 148a, 148b, respectively. The drain supplies 142a, 144a, 142b, 144b and source supplies 146a, 148a, 146b, 148b are coupled to the HVPS 27.

The first connection 147a includes a first pair of switching components 156a and 158a and the second connection 149a includes a second pair of switching components 160a and 162a, respectively. The first and second connections 147b and 149b also include first and second pairs of switching components 156b, 158b and 160b, 162b, respectively. The switching components 156a, 158a, 160a, 162a and 156b, 158b, 160b, 162b can be, for example, transistors, such as metal-oxide semiconductor field-effect transistors (MOSFET), insulated gate bipolar transistors (IGBT), relays, and the like.

The secondary winding 145 includes two output terminals 180 and 182 including a band pass filter 183 coupled therebetween. The first and second connections 147a and 149a are connected in series by a resonant network 150a. The resonant network 150a may be a series resonant network that includes an inductor 153a and capacitors 152a and 154. The network 150a that is arranged in a LCC configuration with the primary winding 143a being coupled between capacitors 152a and 154a. The first and second connections 147b and 149b are similarly connected in series by a resonant network 150b having an inductor 153b with the primary winding 143b coupled between capacitors 152b and 154b.

The output terminals 180 and 182 are coupled to the active and return terminals 30, 32 for outputting electrosurgical energy to the patient. In monopolar configuration, one of the terminals 180 and 182 is be coupled to a monopolar instrument (e.g., the instrument 2a) and the other to the return electrode 6 to provide for the return flow of the electrosurgical energy. In bipolar configuration, one of the output terminals 180 and 182 is coupled individually to an active electrodes of the forceps 10 (e.g., active electrode 14a) and to the return electrode 16.

The configuration of multiple primary windings 143a and 143b coupled to a single secondary winding 145 provides for multi-polar phase-shifted application of RF energy through a single pole (e.g., instruments 2a or active electrode 14a). To ensure that an appropriate amount of current is supplied to the secondary winding 145 from multiple primary windings 143a and 143b, the current passing through each of the primary windings 143a and 143b is monitored and used to ensure that the sum meets the required output power to the tissue being treated.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator, comprising:
  a power supply operable to generate a DC voltage;
  a multi-pole phase-shifted RF output stage coupled to the power supply, the RF output stage including:
    an isolation transformer having a secondary winding; and
    a plurality of dual-pole circuits, each of the plurality of dual-pole circuits including first and second pairs of switching components and a primary winding coupled to the secondary winding; and a controller configured to drive the first and second pairs of switching components of each of the plurality of dual-pole circuits at a predetermined phase-shifted frequency.

2. An electrosurgical generator according to claim 1, wherein the secondary winding includes a pair of output terminals.

3. An electrosurgical generator according to claim 2, wherein the secondary winding includes a band pass filter.

4. An electrosurgical generator according to claim 1, wherein the primary winding includes first and second connections.

5. An electrosurgical generator according to claim 4, wherein the primary winding includes a resonant network interconnecting the first and second connections.

6. An electro surgical generator according to claim 1, wherein the RF output stage is either pulse-width or frequency modulated.

7. An electro surgical system, comprising:
   an electro surgical generator including:
      a power supply operable to generate a DC voltage;
      a multi-pole phase-shifted RF output stage coupled to the power supply, the RF output stage including:
         an isolation transformer having a secondary winding coupled to a plurality of output terminals; and
         a plurality of dual-pole circuits, each of the dual-pole circuits having first and second pairs of switching components and a primary winding coupled to the secondary winding;
      a controller configured to drive the first and second pairs of switching components of each of the plurality of dual-pole circuits at a predetermined phase-shifted frequency; and
   a plurality of active electrodes, each of which is coupled to each of the plurality of output terminals.

8. An electro surgical generator according to claim 7, wherein the secondary winding includes a band pass filter.

9. An electro surgical generator according to claim 7, wherein the primary winding includes first and second connections.

10. An electro surgical generator according to claim 9, wherein the primary winding includes a resonant network interconnecting the first and second connections.

11. An electro surgical generator according to claim 7, wherein the RF output stage is either pulse-width or frequency modulated.

\* \* \* \* \*